United States Patent
Fillières et al.

(10) Patent No.: US 10,154,678 B2
(45) Date of Patent: Dec. 18, 2018

(54) METHOD FOR PRODUCING HYDROLYSED KERATINACEOUS MATERIAL

(71) Applicant: TESSENDERLO CHEMIE N.V., Brussels (BE)

(72) Inventors: Romain Fillières, Vernon (FR); Philippe Blutel, Saint Hilaire le Chatel (FR)

(73) Assignee: TESSENDERLO CHEMIE N.V., Brussels (BE)

( * ) Notice: Subject to any disclaimer, the term of this patent is extended or adjusted under 35 U.S.C. 154(b) by 0 days.

(21) Appl. No.: 14/908,577

(22) PCT Filed: Jul. 29, 2014

(86) PCT No.: PCT/EP2014/066314
§ 371 (c)(1),
(2) Date: Jan. 29, 2016

(87) PCT Pub. No.: WO2015/014860
PCT Pub. Date: Feb. 5, 2015

(65) Prior Publication Data
US 2016/0183560 A1 Jun. 30, 2016

Related U.S. Application Data

(60) Provisional application No. 61/881,537, filed on Sep. 24, 2013.

(30) Foreign Application Priority Data

Jul. 30, 2013 (EP) .................................... 13178511
Apr. 8, 2014 (EP) .................................... 14163922

(51) Int. Cl.
| | | |
|---|---|---|
| *A23J 1/10* | (2006.01) | |
| *A23K 10/26* | (2016.01) | |
| *A23K 20/147* | (2016.01) | |
| *A23K 20/142* | (2016.01) | |
| *A23K 50/40* | (2016.01) | |
| *A23K 50/80* | (2016.01) | |
| *A23J 3/32* | (2006.01) | |
| *A61K 8/98* | (2006.01) | |
| *A61Q 19/00* | (2006.01) | |
| *A61K 8/65* | (2006.01) | |

(52) U.S. Cl.
CPC .. *A23J 1/10* (2013.01); *A23J 3/32* (2013.01); *A23K 10/26* (2016.05); *A23K 20/142* (2016.05); *A23K 20/147* (2016.05); *A23K 50/40* (2016.05); *A23K 50/80* (2016.05); *A61K 8/65* (2013.01); *A61K 8/985* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | |
|---|---|---|
| 2,542,984 A | 2/1951 | Binkley |
| 2,702,245 A | 2/1955 | Mayer et al. |
| 3,923,097 A | 12/1975 | Hovad |
| 4,172,073 A | 10/1979 | Kadri et al. |
| 4,232,123 A | 11/1980 | Braeumer et al. |
| 4,286,884 A | 9/1981 | Retrum |
| 5,772,968 A | 6/1998 | Wolfe |

FOREIGN PATENT DOCUMENTS

| | | | |
|---|---|---|---|
| EP | 0499260 A2 | | 8/1992 |
| WO | 89/11797 A1 | | 12/1989 |
| WO | 90/01023 A1 | | 2/1990 |
| WO | 2011/003015 A1 | | 1/2011 |
| WO | WO 2011/057407 | * | 5/2011 |

OTHER PUBLICATIONS

Moritz et al. ("Indicators of Nutritional Value of Hydrolyzed Feather Meal," 2001 Poultry Science 80:79-86).*
Korremann, Birgitte, "Nutritive Quality of Feather Meal Processed in the Atlas Continuous Hydrolyzer", Sep. 1990.
(Continued)

*Primary Examiner* — Christina Bradley
(74) *Attorney, Agent, or Firm* — Ramin Amirsehhi; Hoyng Rokh Monegier

(57) ABSTRACT

The invention relates to a method for producing digestible keratinaceous material comprising the steps of hydrolysing keratinaceous material in the presence of water in a hydrolyser at elevated temperature and at a pressure between about 2 bar and about 15 bar, and drying the resultant hydrolysed keratinaceous material comprising at least partly insoluble material in a dryer at a temperature/time/pressure combination which limits the drop in pepsin and/or ileal digestibility by less than 10%, and/or such that the pepsin and/or ileal digestibility remains higher than 85%, or such that the pepsin and ileal digestibility remains higher than respectively 75% and 85%. Preferably, the drying of the resultant hydrolysed partly soluble keratinaceous material is performed in a dryer at a temperature such that the keratinaceous material remains at a temperature below 90° C., preferably below 80° C.

14 Claims, No Drawings

(56) References Cited

OTHER PUBLICATIONS

Korremann, Birgitte, "Atlas Hydrolyzer—A New Process for Continuous Hydrolyzation of Keratinous Material", May 10-12, 1989.
Nissen, Hans, "Hydrolising Primer"; Render Aug. 1995, pp. 10-13.
Priority Search Report for EP13178511.5 dated Jan. 24, 2014.
International Search Report for PCT/EP2014/066314 dated Jun. 19, 2015.
International Preliminary Report on Patentability for PCT/EP2014/066314 dated Feb. 2, 2016.
Manning, Mark C. et al, "Stability of Protein Pharmaceuticals", Pharmaceutical Research, vol. 6, No. 11, 1989.
Atlas Industries, "Ring Channel Dryer".
Printout from Wikipedia, "Atlas (virksomhed)"; History of Haarslev Industries, available at: https://da.wikipedia.org/wiki/Atlas_(virksomhed).
N.O. Hansen Argentur ApS, "LT-Fishmeal", available at: http://www.nohansen-argentur.dk/products/fishmeal/lt-fishmeal.html.

\* cited by examiner

METHOD FOR PRODUCING HYDROLYSED KERATINACEOUS MATERIAL

CROSS REFERENCE TO RELATED APPLICATIONS

This application is a 35 U.S.C. 371 National Stage of PCT application number PCT/EP2014/066314 filed on 29 Jul. 2014, which claims priority from EP application number 13178511.5 filed on 30 Jul. 2013, from US application number 61/881,537 filed on 24 Sep. 2013 and from EP application number 14163922.9 filed on 8 Apr. 2014. All applications are hereby incorporated by reference in their entireties.

BACKGROUND OF THE INVENTION

1. Field of the Invention

The invention relates generally to a method for producing hydrolysed keratinaceous material, such as feather meal or meal from hair.

2. Description of the Related Art

As a source of keratinaceous material, animal feathers, hair, hoof, nails and the like can be used. Feathers are by-products from poultry, and hair is a by-product from pigs, cattle, sheep and the like. Also hoofs or nails, that may be grinded, can be used as source of keratinaceous material. Such keratinaceous material has a high protein content, consisting of at least 17 amino acids. However, this keratinaceous material is hardly digestible for animals or humans because of the highly structured polypeptides, with the presence of many (di)sulphide bridges.

Many processes exist for producing (partly) hydrolysed keratinaceous material like feathers or hair, in order to increase the digestibility. Known methods include hydrolysis under pressure while using steam, enzymatic hydrolysis or chemical hydrolysis with e.g. base, acid or other reactive agent.

The keratinaceous material generally is not completely hydrolysed to mono-amino acids to improve the digestibility. In many processes, the resultant product from the partial hydrolysis of the keratinaceous material is partly insoluble in water, and may comprise a mixture of liquid (dissolved) and solid (insoluble) material. Generally, the combined product is converted to a dry solid material by a drying technique. The resultant product generally is not fully digestible for animals, according to for example the pepsin and/or ileal digestibility test. Further, it appears that such products can have anti-nutritional compounds, like lanthionine, in significant amounts.

Several examples of methods for producing partially hydrolysed keratinaceous material like feather meal include U.S. Pat. Nos. 5,772,968, 4,286,884 and 4,172,073. U.S. Pat. No. 4172073 is directed to the water soluble part of the hydrolysed feathers, and is therefore not relevant for the product that is only partially soluble.

Other references exist, that use in addition to steam, also chemical reactants that influence the chemical composition of the hydrolysed material, and cause more complicated work-up processes, as one has to handle the chemicals. Examples of these processes include WO2011/003015, that use oxidizing solutions at low pH, WO1990/01023 that additionally uses hydrogenperoxide, U.S. Pat. No. 4,232,123 that describes an acid hydrolysis followed with an enzymatioc hydrolysis, and EP0499260 that describes hydrolysis with sulphites.

BRIEF SUMMARY OF THE INVENTION

It is an object of the invention to provide a method for producing hydrolysed, partly soluble, solid keratinaceous material, with an improved digestibility.

It is another object of the invention to provide a method for producing hydrolysed, partly soluble, solid keratinaceous material, with a relatively low amount of anti-nutritional compounds like lanthionine.

This object is achieved by a method comprising the steps of partly hydrolysing keratinaceous material in the presence of water with pressure and heat at a pressure below about 15 bar, preferably below about 10 bar, and drying the resultant partially hydrolysed product comprising at least partly insoluble material in a dryer at a temperature/time/pressure combination which limits the drop in pepsin and/or ileal digestibility by less than 10%, and/or such that the pepsin and/or ileal digestibility remains higher than 85%.

Preferably, this object is achieved by a method comprising the steps of partly hydrolysing keratinaceous material in the presence of water with pressure and heat at a pressure below about 15 bar, preferably below about 10 bar, and drying the resultant partially hydrolysed product comprising at least partly insoluble material in a dryer at a temperature/time/pressure combination which limits the drop in pepsin and/or ileal digestibility by less than 10%, wherein the pepsin and ileal digestibility remain higher than respectively 75% and 85%.

As it is clear from the molecular weights of the hydrolysed keratinaceous material, the hydrolysis is not a complete chemical hydrolysis to mono-amino acids, but the hydrolysis comprises the hydrolysation of a substantial number of amide bonds in the polypeptides.

The presence of water during the hydrolysation step is meant to be any of liquid phase water, steam, or water absorbed in the keratinaceous material.

Preferably, the drop in pepsin and/or ileal digestibility is less than 7%, more preferably less than 5%, and/or preferably, the pepsin and/or ileal digestibility remains about 90% or higher, more preferable, about 92% or higher. In a further preferred embodiment, the pepsin and ileal digestibility remain about respectively 80% and 90% or higher, more preferable, about respectively 82% and 92% or higher.

In one embodiment the drying process comprises drying at reduced pressure, such that the temperature of the material remains at a temperature below about 90° C., preferably at a temperature of about 80° C. or lower, and more preferably at about 75° C. or lower, such as for example between about 60 to about 75° C., or for example at a temperature of about 70° C. or lower.

In another embodiment, the drying process comprises effective turbulence of the keratinaceous material in a flow of hot air, such as in a fluidized bed dryer, ring type dryer, rotating drum dryer and the like (hereinafter denoted as "hot air dryer"). In such cases it is important to limit the heat exposure to a minimum. Hence, during a short period of time, e.g. about 60 sec, or about 30 sec, the material may be at a temperature of about 100° C., or about 120° C. Generally, the maximum temperature with short time heat exposure will be about 150° C. or lower, or preferably about 120° C. or lower. A relatively high temperature may be present when relatively low water is present, as the combination of water and heat appears to be most damaging.

It is a further object of the invention to provide a hydrolysed partly soluble keratinaceous material with an improved nutritional value for feed applications.

This object is achieved by providing partly insoluble keratinaceous material with an in vivo digestibility of the Total Nitrogen Matter of more than 80%, preferably of about 82% or higher, as measured on cecectomized roosters, which material comprises an amount of lanthionine of less than about 2 wt %.

Lanthionine is the dimer of cysteine with a single thiobridge. Lanthionine is generally considered as an anti-nutritional compound, and appears to be formed upon drying the partly hydrolysed keratinaceous material. As lanthionine is anti-nutritional, an animal uses a substantial amount of energy to remove such a useless compound from the body. Thereby, lanthionine is counterproductive with respect to the specific aim of supplementing the partly hydrolysed keratinaceous material to an animal.

Lanthionine is one of the most important antinutritional compounds in hydrolysed keratinaceous material. Another antinutritional compound is for example lysinoalanine.

It is an important advantage of the present invention, that the formation of lanthionine is reduced compared to hydrolysed keratinaceous material commonly available in the market, like feather meal.

With measuring the ileal and/or pepsin digestibility, and the amount of lanthionine that is formed during the heating step, the average skilled person will be able to optimize drying conditions such that the advantages of the present invention are achieved.

Preferably, the hydrolysis is performed under pressure, while using steam, in a continuous process. However, batch processes exist as well, and are equally applicable.

In one embodiment of the invention, the drying is preferably performed in a disc dryer, at a pressure below about 0.4 bar (abs), while heating the discs to a temperature lower than about 160° C., preferably lower than 140° C., even more preferably lower than 130° C.

In an alternative embodiment, the dryer is a hot air dryer, preferably a fluidized bed dryer, keeping the temperature of the outlet gaseous stream below about 120° C., preferably during a period of less than about 10 min, and more preferably during a period of less than about 5 min. Alternative hot air dryers are flash dryers or ring type dryers.

DESCRIPTION OF ILLUSTRATIVE EMBODIMENTS

The following is a description of certain embodiments of the invention, given by way of example only and with reference to the examples.

The method according to the present invention comprises the steps of hydrolysing keratinaceous material under pressure with steam at a pressure below about 15 bar, preferably below about 10 bar, and drying the resultant hydrolysed keratinaceous material in a way, such that the keratinaceous meal has a very high digestibility.

One of the steps to achieve such high digestibility is, to keep the keratinaceous material preferably at a temperature below about 120° C., preferably below about 100° C., or below about 80° C. during the drying step. The upper value of the temperature is dependent on the time period that such high temperature is kept.

In one embodiment of the invention, the drying is performed at reduced pressure. Suitable pressures include a pressure below about 0.5 bar (abs), preferably about 0.4 bar or lower. At a pressure of e.g. 0.3 bar, water boils at about 70° C., and thereby the keratinaceous material largely remains at a temperature below the boiling temperature at a certain pressure. An even lower vacuum is also possible, but may have the disadvantage that such low vacuum is relatively expensive to keep. Hence, the reduced pressure generally will be a pressure higher than 10 mbar (abs), and preferably about 100 mbar or higher.

In order to allow an economical process, it is important that the equipment or plant for treating the keratinaceous material is able to process about 2 ton per hour or more, preferably between about 4 and about 15 tons. In view of the required high amount of throughput, several drying techniques, like for example drying overnight in a stove are impossible to use. Furthermore freeze drying is preferably not performed, and such drying method preferably is excluded because this is relatively expensive.

Hence, in the present invention, preferably, drying processes are excluded that comprise non-stirred/non-moving drying. Non-stirred or non-moving drying is understood to be a method wherein the keratinaceous material stays substantially on a fixed place, like when an amount of feather meal is placed in an oven at e.g. 50° C. overnight to dry the product or when the product is placed in a freeze drying tunnel.

The keratinaceous material, like feather or hair, is generally wet before supplying the material to the hydrolyser. The amount of water generally is between about 30 and about 80 wt %, and more preferably between about 50 and about 75 wt %, and most preferably, between about 65 wt % and about 75 wt %.

The keratinaceous material may be milled or crushed to reduce the size. Generally, size reduction for hair of pigs or cattle is not very useful.

The hydrolyser generally works at a pressure of about 15 bar or below, preferably about 10 bar or below, as higher pressure is increasingly costly. The pressure generally is about 2 bar or higher. Higher pressure is preferred, to increase the degree and speed of hydrolysation. Hence, the pressure preferably is about 4 bar or higher, and even more preferable, about 6 bar or higher. Generally, the pressure will be about 9 bar or lower. The pressure is given as bar absolute.

The hydrolysis will be performed in a hydrolyser, generally called a steam-hydrolyser. The hydrolyser is essentially a stirred vessel, and may be batch or continuous. The hydrolyser preferably allows a continuous process, and is a stirred tube like vessel like an extruder or a vertical stirred vessel. Stirring preferably is done with a slowly propelling screw type of mixer, paddles or the like.

The hydrolysis step generally will be performed for a period between about 5 and about 180 min, preferably between about 10 and about 60 min. Lower pressure generally requires longer reaction times.

Hence, the time/pressure window in general would be between about 2 to about 15 bar during about 5 min. to about 3 hr, preferably between about 2 and about 10 bar, and more preferably between about 4 to about 9 bar during about 10min to about 1 hr. The temperature follows from the (saturated) steam pressure. Thus, the temperature at about 2 bar is about 120° C., 4 bar corresponds to 144° C., and 9 bar to 175° C., the temperature at about 10 bar is about 180° C., and about 15 bar corresponds to about 200° C.

The steam may be directly injected, or may be used for indirect heating. Indirect heating may also be applied with hot oil coils. Ultimately, the pressure should be as required, and the amount of water preferably is such, that saturated steam is present at the chosen pressure and temperature. Preferably, the total amount of steam present is about 200 gram of steam or more per kg of feather and more preferably 300 gram per kg of feather. More live steam can be used instead of indirect steam to increase the degree of hydrolysis.

The hydrolysis with such technique always results in only a partial hydrolysis. Hence, the resulting mixture comprises oligo-peptides, and polypeptides.

The hydrolysed keratinaceous material will be dried after the (partial) hydrolysis. This drying generally is done in a number of steps. The first step comprises bringing the mixture leaving the hydrolyser to atmospheric pressure, while evaporating part of the water.

Optionally, it is possible to press part of the water from the keratinaceous material to bring the water content—for example—from about 55 wt % or higher to about 45 wt % or lower.

The water pressed from the keratinaceous material after the hydrolysis step is generally referred to as stick water. The stick water generally contains some fatty materials and sediments, which fatty material can be removed by centrifugation if desirable.

Removing the fat from the crude stick water will enable the production of a low fat keratinaceous material such as feather meal. The amount of fat in the crude stick water may be for example 30% or more, like for example about 50% or more of the total fat present in the crude feathers. With centrifugation, most fat can be removed from the stick water. In this way, about 30% or more, preferably about 50% or more of the total fat will be reduced. Generally, not all fat can be removed in this way, and for example less than about 70% of the fat is removed.

The stick water (defatted or not-defatted) can be further concentrated by means of evaporators, such as for example multiple effect falling films, rising films or whipped film evaporators, preferably at reduced pressure, using the hot vapours of the dryer in a combined heat recovery system. Such evaporation will raise the dry substance of the stick waters from about 5 to 10% up to about 25 to 40%. This concentrate, rich in solubilized and insoluble proteins can be re-injected into the dryer, and processed with the solid keratinaceous material.

In an alternative embodiment, the stick water can be dried as such using suitable drying methods. Suitable drying techniques include a plurality of techniques, such as for example drum drying and spray drying. When spray drying is used, it is preferred to have the fatty materials and sediments removed from the stick water. The dried keratinaceous material can have suitable particle sizes with a D50 between about 50 μm to about 2 mm, preferably between about 0.1 and about 1 mm. The product may be granulated to any suitable particle size. Such use of stick water has the advantage of providing a product with a very high digestibility, such as preferably more than about 95% ileal and/or pepsin digestibility, more preferably about 97% or more.

Therefore, the present invention also relates to a process for preparing highly digestible keratinaceous material in powder (or dry) form, by hydrolyzing keratinaceous material as described, and separating a water phase (or liquid phase) from solid keratinaceous material in a press, and drying the water (or liquid) phase to obtain a product in powder form, having an ileal and/or pepsin digestibility of more than about 95%.

Further, the present invention relates to a process for preparing highly digestible keratinaceous material in a dry form with a reduced fat content, by hydrolyzing keratinaceous material in the presence of water, in a hydrolyser with heat and at a pressure between about 2 bar and about 15 bar, preferably between about 2 bar and about 10 bar, separating a liquid phase from solid keratinaceous material in a press, centrifuging the liquid phase to separate an aqueous phase containing solubilized proteins, a fat phase and residual solids and reincorporating the defatted aqueous phase and the residual solids into the keratinaceous material and further drying the material to produce a low fat highly digestible feather meal.

The resultant, still moist keratinaceous material needs to be dried to a moisture content of about 12 wt % or less, preferably about 8 wt % or less. Drying to an amount of water lower than about 3 wt % generally is not necessary, but would not harm. Drying is most preferably performed till a moisture content of about 4 to 8 wt %. The amount is stated relative to the total product.

Drying appears to be a crucial step in the quality of the keratinaceous material such as feather meal. It appears that common drying techniques cause the digestibility to be reduced considerably.

According to GePro, a company selling feather meal, flash drying (hot air drying) results in better in vitro digestibility. The ileal digestibility was found to be less than 85%. The pepsin digestibility about 70% to about 80%. Yet, further improvement is aimed for.

The present inventors found that further improvement was possible, by using for example a conventional disc dryer at reduced pressure and reduced temperature, or when for example using a fluidized bed dryer.

Thus, the present invention provides a method in which partly hydrolysed keratinaceous material is provided with higher in vitro and/or in vivo digestibility.

With the method of the present invention, it is possible to obtain hydrolysed, partly insoluble keratinaceous material with a moisture content of less than about 8 wt % and an in vivo digestibility of the Total Nitrogen Matter of about 80% or higher (digestibility measured on cecectomized roosters).

Preferably, the amount of lanthionine in the hydrolysed keratinaceous material is about 2 wt % or less, preferably about 1.7 wt % or less, or preferably about 1.5 wt % or less, more preferably about 1.2 wt % or less.

The hydrolysed keratinaceous material is at least partly insoluble in water, when 1 gram is put in 2 ml of water particles and fibrous material is seen with the eye.

In a quantitative test, the amount of insoluble material can be measured. Such a test can be performed by dissolving 100 g feather meal in 1000 mL of water by stirring for 15 minutes in water at 20° C. The mixture is filtered, the filtrate and solid material weighed and dried, and the dried material weighed.

In the quantitative test, the amounts of solids is about 60 wt % or more, preferably about 80 wt % or more, and even more preferably about 90 wt % or more.

The amount of soluble material according to this test may be about 1 wt % or more, like about 2, about 3 wt %, about 4 or about 5 wt %. In case the stick water is processed separately, the amount of insoluble material may be between 100-98 wt %.

Despite the low solubility in water, it is possible to measure the molecular weight distribution of at least part of the keratinaceous material preferably in a solvent that is designed to dissolve proteinous material better than water. The most commonly used method is HPLC with water/acetonitril as a solvent with a trilfuoroacetic acid (TFA; 0.1 wt %) and a SEC a column. The keratinaceous material may be better soluble, or completely soluble in said solvent. The partially hydrolysed material shows a broad peak. The molecular weight distribution is in this field generally not denoted as Mn/Mw, as not all material may be dissolved. It is anyhow possible to state which part of the material measured in the HPLC has a certain molecular weight.

In a preferred embodiment of the invention, the dissolved part of the hydrolysed keratinacious material consists for about 70 wt % or more of material having a molecular weight of about 5000 dalton or less, and more than 30 wt % of the materials has a molecular weight of about 1000 dalton or less.

In another preferred embodiment, which may be combined with the embodiment in the preceding paragraph, the amount of material of a molecular weight higher than about 5000 dalton is about 10 wt % or more, preferably about 20 wt % or more.

After the partial hydrolysation, the hydrolysed keratinaceous material is dried to a moisture content of about 12 wt % or lower, or of about 8% or lower, with a method allowing low heat damage. The low heat damage provides for a low or absent reduction in digestible material, and the final pepsin and/or ileal digestibility is still higher than 85%. Preferably, the pepsin and ileal digestibility remain higher than respectively 75% and 85%. The final pepsin and/or ileal digestibility may be about 85% or higher, or 90% or higher.

The drying preferably is performed in a dryer at a temperature/time/pressure combination which limits the drop in pepsin and/or ileal digestibility by less than about 10%, and/or such that the ileal and/or pepsin digestibility remains higher than about 90%. In a further preferred embodiment, the pepsin and ileal digestibility remain about respectively 80% and 90% or higher, more preferable, about respectively 82% and 92% or higher.

Preferably, the drop in pepsin and/or ileal digestibility is about 7% or less, more preferably about 5% or less, and/or preferably, the ileal digestibility remains about 90% or higher, more preferably, about 92% or higher.

The further drying is preferably done at reduced pressure, or in a fluidized bed dryer, such that the heat damage, measured as reduced digestibility is such that the final product still has a pepsin and ileal digestibility of more than respectively about 80% and 90%.

Achieving such low damage by heat is unprecedented in the production of feather meal, which production is already done for over 60 years (see e.g. U.S. Pat. No. 2,542,984).

One of the steps to achieve such high digestibility is, to keep the keratinaceous material preferably at a temperature below about 120° C., preferably below about 100° C., or below about 80° C. The upper value of the temperature is dependent on the time period that such high temperature is kept.

In one embodiment of the invention, the drying is performed at reduced pressure. Suitable pressures include a pressure below about 0.5 bar (abs), preferably below about 0.4 bar. At a pressure of 0.3 bar, water boils at about 70° C., and thereby the keratinaceous material largely remains at a temperature below such temperature. An even lower vacuum is also possible, but may have the disadvantage that such low vacuum is relatively expensive to keep. Hence, the reduced pressure generally will be a pressure higher than about 10 mbar (abs), preferably at about 100 mbar or higher.

In another embodiment, the drying process comprises effective turbulence of keratinaceous material, in a fluidized bed dryer, ring dryer or for example a flash dryer. In such cases it is important to limit the heat exposure to a minimum. Hence, during a short period of time, e.g. about 60 sec, or about 30 sec, the material may be at a temperature of about 100° C., or about 120° C. Generally, the maximum temperature with short time heat exposure will be about 150° C. or lower, or preferably about 120° C. or lower. A relatively high temperature may be present when relatively low water is present, as the combination of water and heat appears to be most damaging.

Hence, the temperature/time window may be between about 60 to about 150° C. and between about 30 sec to about 2 hr, being dependent on the damage done by heating the moist keratinaceous material. Lower temperature allows longer drying times, and require generally, reduced pressure. Higher temperatures require short drying times, and generally do not require reduced pressure.

The digestible keratinaceous material such as feather meal comprises at least 17 amino acids, such as very valuable amino acids like cysteine and tyrosine.

Preferably, the amount of cysteine is about 2 wt % or more, more preferably about 3 wt % or more, even more preferably about 4 to 5 wt % or more. The wt % is expressed as relative to the total protein content.

The dried product may be milled and/or agglomerated to a suitable particle size. The particles generally are smaller than a few mm, and larger than 20 µm, in order to have a free flowing powder that can be easily processed. Generally, the particle size will be between 0.01 and 2 mm.

The digestible keratinaceous material such as feather meal can be used as feed, or feed supplement, such as for example for petfood and/or for aquaculture, or as additive in cosmetics.

Dried highly digestible feather meal is in particular very useful for feed or feed additive, like as feed for fish and for shrimp. It can replace expensive and non-sustainable fish meal in such aquaculture diets. Replacement of fish meal will depend on the species, and exemplary amounts include up to 40% in salmon feed and up to 75% in African catfish. With the very good quality feather meal of the present invention, it is expected that even higher amounts of replacement is possible.

The digestible keratinaceous material such as feather meal can be packed in small bags, big bags or shipped in bulk container.

Measurement Methods

The following methods were used in the examples, and are suitable as methods to measure the parameters stated in the description and the claims:

Weight percentage (wt %) moisture: the moist keratinaceous material is dried overnight in a vacuum stove at reduced pressure and with a siccative. The material is weighted before and after the drying step, and the amount of moisture is calculated with using the initial measured weight as 100% while assuming that all the volatile material is water.

HPLC and Mw determination: Standard HPLC equipment can be used. The solvent for the keratinaceous material is MilliQ water, acetonitrile and trifluoroacetic acid (TFA) at 0.1 wt %. As a column, a Tosoh Bioscience Silica Column TSK G2000 SWXL 5 µm and Tosoh Bioscience Guard Column TSK-Gel SWXL 7 µm can be used, or comparable columns. The mobile phase is a trifluoroacetic acid 0.1 wt %, containing 15% acetonitrile ($CH_3CN$). The recording is done with a UV detector at 214 nm. The column can be calibrated with a mixture of bacitracin, insulin, alpha-lacto-albumin, beta-lacto-globulin and tryptophan.

Solubility of the keratinaceous material is qualitatively determined by dissolving 1 gram of keratinaceous material in 2 ml water at 20° C. The transparency of the liquid is determined by the human eye.

In a quantitative test the solubility of the keratinaceous material can be performed as follows: 100 g of feather meal is dissolved in 1000 mL of water by stirring for 15 minutes in water at 20° C. The mixture is filtered over a 350 µm filter under pressure. The filtrate and the solids on the filter are dried and their weight measured. In this analysis, one would correct for the moisture content of the materials, i.e. the moisture content of the feather meal should be measured as well. Further, one should correct for the amount of soluble material that remains in the wet solids which are filtered out.

Pepsin digestibility is measured according to ISO 6655 (August 1997); 0.02% pepsin.

Ileal digestibility (also named "Boisen digestibility") is measured according to S. Boisen, 2007 ("In vitro analysis for determining standardized ileal digestibility of protein and amino acids in actual batches of feedstuffs and diets for pigs"; Livestock Science (2007) 309:182-185.).

In vivo digestibility of the Total Nitrogen Matter has been determined on cecectomized roosters, according to Johnson et al., 1998. "Effects of species raw material source, ash content, and processing temperature on amino acid digestibility of animal by-product meals by cecectomized roosters and ileally cannulated dogs" Journal of Animal Science; 76:1112-1122.

The percentage of lanthionine (abbreviated as LAN in the examples) is determined with standard HPLC methods.

Further modifications in addition to those described above may be made to the materials and methods described herein without departing from the spirit and scope of the invention. Accordingly, although specific embodiments have been described, these are examples only and are not limiting upon the scope of the invention.

EXAMPLES

Example 1 and Comparative Experiments A-C

In a hydrolyser, working at 7 bar and saturated steam, feathers from chicken with a moisture content of 65 wt % were treated for 25 min. The partly hydrolysed fibre was brought to atmospheric pressure through a let-down valve, and the fibrous mass, containing about 55% of water was pressed in a screw press to remove water. The residual water in the feather meal was about 45 wt %.

The partly hydrolysed feather meal was dried in a number of different ways, with a classical disc dryer at 170° C. (8 bar pressure steam inside the disc), for about 1 hr (Comp Exp A), and for about 0.8 hr (Comp Exp B) (both comparative experiments, according to the prior art), a hot air dryer (Comp Exp C) (using a temperature of the air of for 80 sec at 270° C. and for 120 sec at 80° C.), and a disc dryer at 300 mbar pressure (abs) (Example 1). In the last mentioned drying method (for example 1), the feather meal did not reach temperatures higher than about 70° C.

TABLE 1 characteristics of dried feather meal

| | Comp Exp A | Comp Exp B | Comp Exp C | Example 1 |
|---|---|---|---|---|
| Process Characteristic | | | | |
| Hydrolyser | Batch | Continuous | Continuous | Continuous |
| Dryer | Disc; 1 hr | Disc; 0.8 hr | Hot air | Low temp disc (vacuum) |
| Meal quality | | | | |
| Pepsin digestibility | 54 | 64 | 74 | 85 |

TABLE 1-continued characteristics of dried feather meal

| | Comp Exp A | Comp Exp B | Comp Exp C | Example 1 |
|---|---|---|---|---|
| Ileal digestibility | 74 | 81 | 84 | 93 |
| Molecular weight | | | | |
| <5000 | 84 | 88 | 82 | 85 |
| <1000 | 57 | 42 | 48 | 56 |
| <500 | 45 | 27 | 29 | 42 |
| Percentage LAN | 2.3 | 2.2 | Nd | 1.3 |

Nd: not determined

The solubility of the feather meal obtained in example 1 was measured. 100 g feather meal with a moisture content of 4.81 wt % was dissolved in 1000 mL of water by stirring for 15 minutes in water at 20° C. The mixture was filtered over a 350 µm filter under pressure. The filtrate (923.5 g) and the solids on the filter were dried and their weight measured and were as follows: solids on filter (wet) 148.1 gr; solids on filter dry: 90.54 g. The filtrate contained 3.42 g solid material. Hence, the moisture in the solid material (which was 57.56 g) contained 0.21 g soluble product. Hence, from the 95.19 g dry feather meal, 3.63 g (3.42 g+0.21 g) was soluble. This amounts to 3.8 wt % relative to the feather meal.

Example 2

In a batch hydrolyser, working at 7 bar and saturated steam, feathers from chicken with a moisture content of 70 wt % were treated for 25 min. The partly hydrolysed fibre was brought to atmospheric pressure through a let-down valve, and the fibrous mass contained 65% of water.

The partly hydrolysed feather meal was dried in a fluidized bed dryer. The inlet temperature of the hot air was 140° C.; the outlet temperature was about 85° C. The feather meal did not reach temperatures higher than about 80° C. for any substantial amount of time. Drying till a moisture content of about 7 wt % took about 8 min. The in-vivo digestibility of the Total Nitrogen Matter (TNM) measured on cecectomized roosters was 80% and the in-vitro ileal digestibility of the TNM was 88%.

Example 3

In a continuous hydrolyser, working at 5 bars and saturated steam, mixed poultry feathers, comprising chicken feathers and turkey feathers, with a moisture content of about 70% were treated for about 20 minutes at a flow rate of 4 tons/hour. At the outlet of the hydrolyser, the moisture content of the hydrolyzed feathers was 50-55% and the ileal and pepsin digestibility were respectively 95% and 88%. The hydrolyzed feathers were dried at reduced pressure in a disc dryer at 300 mbar pressure (abs) at a flow rate of 4 tons/hour. The ileal and pepsin digestibility of the dried feather meal (2.5% moisture) were respectively 90% and 81%. The drop in pepsin and ileal digestibility in the drying step was therefore less than 10%. The in-vivo digestibility test of this feather meal on cecectomized roosters showed a digestibility of 83%. The amount of lanthionine was 1.66 wt %.

Conclusion

The examples are illustrative only, but the tests show that with the hydrolysis and drying as performed with the present invention, highly digestible keratinaceous meal, like feather meal is obtained.

What is claimed is:

1. A method for producing digestible keratinaceous material, comprising the steps of hydrolysing keratinaceous material in the presence of water, in a hydrolyser with heat and at a pressure between about 2 bar and about 15 bar, and drying the hydrolysed keratinaceous material comprising at least partly insoluble material in a dryer at a temperature/time/pressure combination which limits the drop in pepsin and/or ileal digestibility by less than 10%, and/or such that the pepsin and/or ileal digestibility remains higher than 85%, or which limits the drop in pepsin and/or ileal digestibility by less than 10%, wherein the pepsin and ileal digestibility remain higher than respectively 75% and 85%, wherein an amount of more than about 2 tons of keratinaceous material is processed per hour and the drying method is not a non-stirred/non-moving drying method, and wherein the amount of insoluble material is 60 wt% or more if 100 g keratinaceous material is dissolved in 1000 mL of water at 20° C. and stirring for 15 min.

2. A method for producing digestible keratinaceous material, comprising the steps of hydrolysing keratinaceous material in the presence of water, in a hydrolyser with heat and at a pressure between about 2 bar and about 15 bar, and drying the hydrolysed keratinaceous material comprising at least partly insoluble material in a dryer at a temperature such that the keratinaceous material remains at a temperature below about 90° C., wherein an amount of more than about 2 tons of keratinaceous material is processed per hour and the drying method is not a non-stirred/non-moving drying method, and wherein the amount of insoluble material is 60 wt% or more if 100 g keratinaceous material is dissolved in 1000 mL of water at 20° C. and stirring for 15 min.

3. The method according to claim 1, wherein the hydrolysis is performed in a continuous hydrolyser.

4. The method according to claim 1, wherein the keratinaceous material is supplied to the hydrolyser with a moisture content of about 30 to about 80 wt% relative to the weight of moisture plus keratinaceous material.

5. The method according to claim 1, wherein the dryer is a disc dryer processing at a pressure between about 10 and about 500 mbar (abs).

6. The method according to claim 1, wherein the drying is performed in a flow of hot air.

7. The method according to claim 1, wherein the dried digestible keratinaceous material has a moisture content of below about 12 wt%.

8. The method according to claim 2 wherein the drying step is performed at a temperature/time/pressure combination which limits the drop in pepsin and/or ileal digestibility by less than about 10%, and/or such that the pepsin and/or ileal digestibility remains higher than about 85%, or which limits the drop in pepsin and/or ileal digestibility by less than 10%, wherein the pepsin and ileal digestibility remain higher than respectively about 75% and about 85%.

9. The method according to claim 1, wherein the drying step is performed at a temperature/time/pressure combination which limits the drop in pepsin and/or ileal digestibility by less than about 7%, and/or such that the pepsin and/ ileal digestibility remains higher than about respectively 80% and 90%.

10. The method according to claim 1, wherein said method comprises separating a liquid phase containing solubilized proteins from the insoluble material in a press, and drying separately the liquid phase to obtain a product in powder form, having an ileal and/or pepsin digestibility of more than about 95%.

11. The method according to claim 1, wherein said method comprises separating a liquid phase from the insoluble material in a press, centrifuging the liquid phase to separate an aqueous phase containing solubilized proteins, a fat phase and residuals solids, reincorporating the defatted aqueous phase and the residuals solids into the keratinaceous material and further drying the material to produce a low fat highly digestible feather meal.

12. The method according to claim 2, wherein the hydrolysis is performed in a continuous hydrolyser.

13. The method according to claim 2, wherein the keratinaceous material remains at a temperature below about 80° C.

14. The method according to claim 1, wherein the drying is performed in a fluidized bed dryer, ring-type dryer, or rotating flash dryers with a flow of gas at a temperature of about 150° C. or lower.

* * * * *